United States Patent
Boehm et al.

(10) Patent No.: US 10,568,721 B2
(45) Date of Patent: Feb. 25, 2020

(54) METHOD FOR PRODUCING A DENTURE BASE SEMI-FINISHED PRODUCT

(71) Applicant: Kulzer GmbH, Hanau (DE)

(72) Inventors: Uwe Boehm, Hanau (DE); Marco Spatz, Sailauf (DE)

(73) Assignee: Kulzer GmbH, Hanau (DE)

(*) Notice: Subject to any disclaimer, the term of this patent is extended or adjusted under 35 U.S.C. 154(b) by 253 days.

(21) Appl. No.: 15/313,699

(22) PCT Filed: May 22, 2015

(86) PCT No.: PCT/EP2015/061443
§ 371 (c)(1),
(2) Date: Nov. 23, 2016

(87) PCT Pub. No.: WO2015/181093
PCT Pub. Date: Dec. 3, 2015

(65) Prior Publication Data
US 2017/0202650 A1 Jul. 20, 2017

(30) Foreign Application Priority Data
May 27, 2014 (DE) .................. 10 2014 107 418

(51) Int. Cl.
*A61C 9/00* (2006.01)
*A61C 13/00* (2006.01)
(Continued)

(52) U.S. Cl.
CPC .......... *A61C 9/004* (2013.01); *A61C 13/0001* (2013.01); *A61C 13/0004* (2013.01);
(Continued)

(58) Field of Classification Search
CPC ..... A61C 9/004; A61C 13/0004; A61C 13/01; A61C 13/0001; A61C 13/0022;
(Continued)

(56) References Cited

U.S. PATENT DOCUMENTS

| 8,206,152 B2 | 6/2012 | Holzner et al. |
| 8,506,299 B2 | 8/2013 | Gaertner et al. |

(Continued)

FOREIGN PATENT DOCUMENTS

| DE | 202006006286 U1 | 8/2007 |
| DE | 102009056752 A1 | 6/2011 |

(Continued)

OTHER PUBLICATIONS

Office Action in JP Application No. 2016-569758 dated Aug. 30, 2017, 8 pages.
(Continued)

*Primary Examiner* — Nathan L Laughlin
(74) *Attorney, Agent, or Firm* — Marshall, Gerstein & Borun LLP

(57) ABSTRACT

The invention relates to a method for producing a denture base semi-finished product with the following steps:
1) Recording and digitalizing the oral cavity situation of a patient, wherein a digital three-dimensional oral cavity model of the patient is produced, or providing a digital three-dimensional oral cavity model of the oral cavity situation of a patient;
2) Implementing a first calculation in which a digital three-dimensional first model (A) of a denture base is calculated, wherein the oral cavity model of the oral cavity situation is used as a basis for the first calculation;
3) Conducting a second calculation, in which a digital three-dimensional second model (B) of a denture base semi-finished product is calculated from the first model (A) of the denture base, wherein volume is added at least in sections to the three-dimensional model (A) of the denture base; and
4) Producing the denture base semi-finished product with a Rapid Prototyping method, wherein with the Rapid Proto-
(Continued)

typing method, a CAM method is used and the digital three-dimensional second model (B) of the denture semi-finished product is used as the basis for the CAM method. The invention also relates to a device for implementing such a method and a denture base semi-finished product produced using such a method.

29 Claims, 1 Drawing Sheet

(51) Int. Cl.
  *A61C 13/107* (2006.01)
  *A61C 13/01* (2006.01)
(52) U.S. Cl.
  CPC ...... *A61C 13/0006* (2013.01); *A61C 13/0013* (2013.01); *A61C 13/0015* (2013.01); *A61C 13/0018* (2013.01); *A61C 13/0019* (2013.01); *A61C 13/0022* (2013.01); *A61C 13/01* (2013.01)
(58) Field of Classification Search
  CPC ............ A61C 13/0018; A61C 13/0015; A61C 13/0013; A61C 13/0006
  See application file for complete search history.

(56) References Cited

U.S. PATENT DOCUMENTS

| | | | |
|---|---|---|---|
| 9,295,534 B2 | 3/2016 | Ruppert et al. | |
| 2005/0023710 A1 | 2/2005 | Brodkin et al. | |
| 2005/0186540 A1* | 8/2005 | Taub | A61C 13/0004 433/223 |
| 2010/0291505 A1 | 11/2010 | Rawley et al. | |
| 2012/0179281 A1* | 7/2012 | Steingart | A61C 13/0004 700/97 |
| 2012/0261848 A1* | 10/2012 | Haraszati | A61C 13/0004 264/17 |
| 2012/0276502 A1* | 11/2012 | Marshall | G05B 19/4099 433/199.1 |
| 2013/0326878 A1 | 12/2013 | Boehm et al. | |
| 2014/0008826 A1 | 1/2014 | Dierkes et al. | |
| 2014/0113248 A1 | 4/2014 | Johansson et al. | |
| 2014/0272787 A1* | 9/2014 | Ginsburg | A61C 13/0004 433/171 |
| 2014/0308624 A1* | 10/2014 | Lee | A61C 9/0006 433/37 |
| 2014/0317930 A1 | 10/2014 | Klingenburg et al. | |

FOREIGN PATENT DOCUMENTS

| | | |
|---|---|---|
| DE | 102012011371 A1 | 12/2013 |
| EP | 1444965 A2 | 8/2004 |
| WO | WO-91/07141 A1 | 5/1991 |
| WO | WO-2008/081003 A1 | 7/2008 |
| WO | WO-2011/124474 A1 | 10/2011 |
| WO | WO-2013/068124 A2 | 5/2013 |
| WO | WO-2013/124452 A1 | 8/2013 |

OTHER PUBLICATIONS

Search Report in International Application No. PCT/EP2015/061443 dated Sep. 8, 2015, 6 pages.
Office Action in German Application No. 10 2014 107 418.1 dated Apr. 10, 2015, 6 pages.
International Preliminary Report on Patentability and Written Opinion in International Application No. PCT/EP2015/061443 dated Dec. 8, 2016, 9 pages.

* cited by examiner

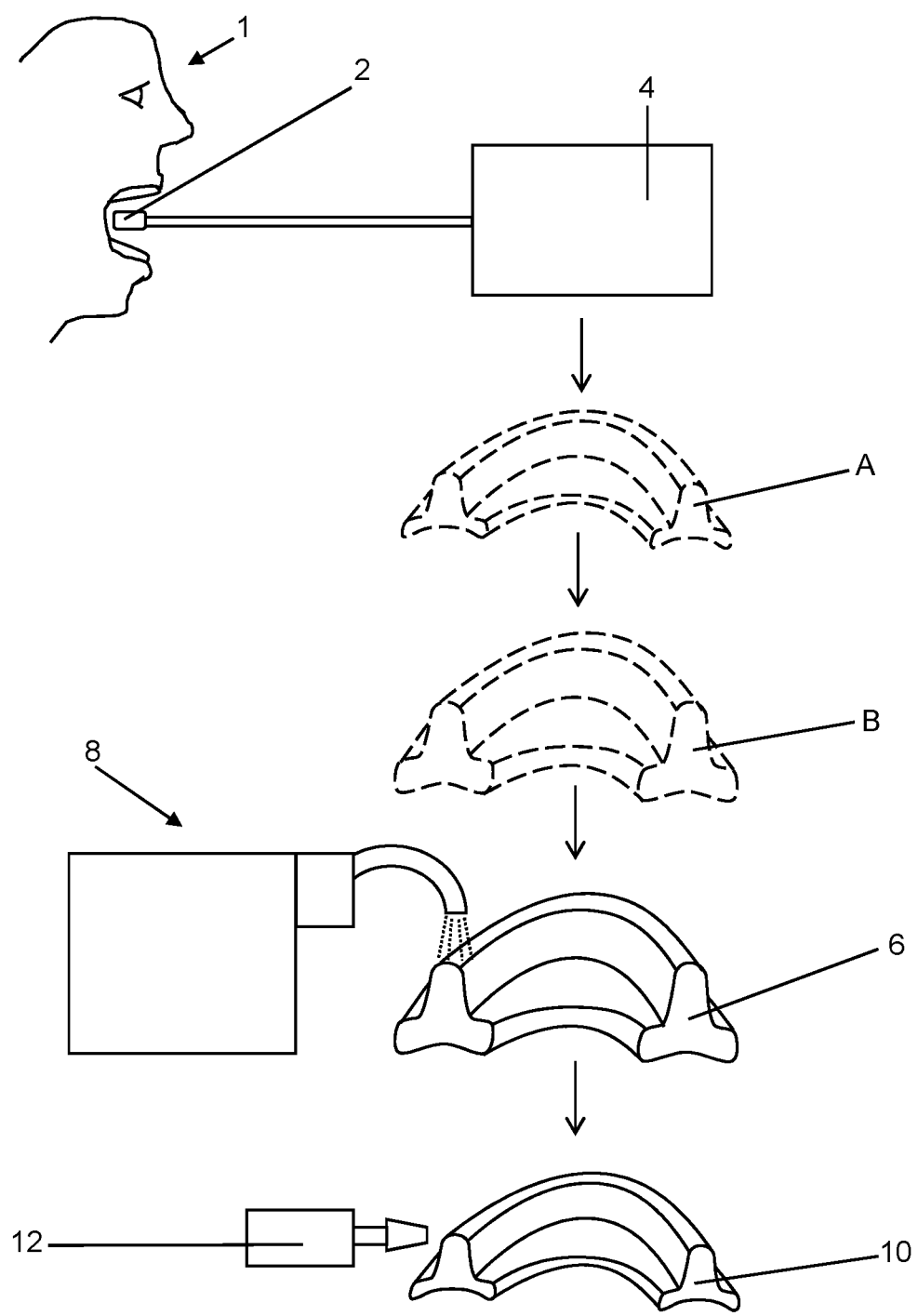

METHOD FOR PRODUCING A DENTURE BASE SEMI-FINISHED PRODUCT

The invention relates to a method for producing a denture base semi-finished product and a method for producing a denture base.

The invention also relates to a computer-controlled device for implementing a method for producing a denture base semi-finished product or a method for producing a denture base and a denture semi-finished product and a denture base produced using such methods.

The invention thus relates to the production of prefabricated semi-finished products for the production of individualized denture bases for further processing for partial plastic dentures (partial dentures) and total plastic dentures (total dentures), which are machine-produced using the CAM method (CAM—Computer-Aided Manufacturing). The individualized denture bases can also be used as a working model made of wax, with which a fitting is conducted with a patient, and which serves as the basis for the production of a partial plastic denture (partial dentures) or a total plastic denture (total dentures). Here, the denture base semi-finished products, as well as the denture bases and dentures, are constructed in a computer-supported manner using CAD methods (CAD—Computer-Aided Design).

The standard route is the analog production of dentures. In order to produce the denture base, an analog method is currently usually used, in which first, an impression is taken of the toothless jaw of the patient. From this impression, a mold is produced which is poured with a gum-colored plastic. After the plastic has hardened, it is further processed in order to obtain the desired form. The separately produced prosthetic teeth are then inserted.

In order to produce the denture, teeth are manually and individually set down on a wax base. In the next step, this wax denture is embedded in plaster in a cuvette in order to then wash out the wax base with hot water after the plaster has hardened and create a hollow space for the denture plastic. The prosthetic teeth remain in the plaster during this process. A corresponding plastic is injected into the hollow space and the denture is obtained after the plastic has hardened.

During the setting down of the prefabricated teeth, these are adapted to the respective mouth situation of the patient and ground by the dental technician; and also by the dentist if necessary.

Such a method is known from WO 91/07141 A1, wherein with this method, a denture base is milled from a plastic block on the basis of an impression. First methods are already available such as those known from DE 10 2009 056 752 A1 or WO 2013 124 452 A1, in which a partial or total denture is digitally designed and produced using CAD-CAM methods. Optimized methods for producing dentures with CAD-CAM methods are also known from EP 1 444 965 A2. A milling block with pre-formed prosthetic teeth is known from WO 2013 068 124 A2. The disadvantage here is that the prosthetic teeth consist of the same material as the base, and if damage occurs, the entire jaw must be replaced and the finished constructed denture can only be adapted to the needs of the patient (for example with regard to the tooth color or occlusion and tooth position) with a high degree of effort. A further disadvantage is that different demands are made on the base and the prosthetic teeth (or the denture tooth crown), but that they are made of the same material. Thus, the tooth is primarily intended for chewing and should remain undamaged while doing so. By contrast, the base should distribute the forces arising via the mucous membrane. This can lead to problems if only one material is used. In order for the milling block to remain usable for the largest number of different denture forms possible, it must be large and thus, in most cases, large quantities of the material must be removed from the milling block. Alongside the waste of material removed, the time-consuming milling work and wear of the milling tools are also disadvantageous.

A round blank for producing a denture is known from DE 20 2006 006 286 U1. This blank (or so called round) is tensioned in a CAM milling machine and automatically milled off on the basis of a CAD model. Current methods mill a denture base which is only 2 mm to 3 mm thick from such a full block (the round). With this method, too, the disadvantages are on the one hand a very high degree of material waste, which can easily exceed 90% depending on the anatomical situation of the respective patient. On the other, this leads to time-intensive processing times by the CAM device, since a great deal of material must be removed. Furthermore, the wear of the respective milling tools is relatively high, which leads to an increase in the costs of operating the mill.

The disadvantage here is further that it takes a relatively long time until the denture base has been produced. Additionally, the milling head is subject to wear through processing the blank, and must be replaced at regular intervals. The milled-off material (the milling chips) must be disposed of or recycled.

The object of the invention is thus to overcome the disadvantages of the prior art. In particular, a method, a raw material (component) and/or a product are to be provided with which the simplest possible, complete and low-cost production of the denture base and thus of the denture is enabled. The milling head and/or the tool for conducting the subtractive CAM method should here be subjected to as little wear as possible. Additionally, the production of the denture base should be completed as quickly as possible. At the same time, the denture base to be produced should however be adaptable to the individual needs of the patient using modern CAD-CAM methods and be possible to produce automatically.

The objects of the invention are attained by means of a method for producing a denture base semi-finished product with the following steps:

1) Recording and digitalizing the oral cavity situation of a patient, wherein a digital, three-dimensional oral cavity model of the patient is generated, or providing a digital three-dimensional oral cavity model of the oral cavity situation of a patient;

2) Implementing a first calculation in which a digital three-dimensional first model (A) of a denture base is calculated, wherein the oral cavity model of the oral cavity situation is used as the basis for the first calculation;

3) Implementing a second calculation in which a digital three-dimensional second model (B) of a denture base semi-finished product is calculated from the first model (A) of the denture base, wherein volume is added at least in section to the three-dimensional model (A) of the denture base; and 4) Production of the denture base semi-finished product using a Rapid Prototyping method, wherein with the Rapid Prototyping method, a CAM method is used and the digital three-dimensional second model (B) of the denture base semi-finished product is used as a basis for the CAM method.

For reasons of clarity, it should be noted that with the method according to the invention, there is only one model respectively of the denture base, namely the first model (A)

and one model of the denture base semi-finished product, namely the second model (B). Thus there is only one set of data which forms the model (A) of the denture base and one set of data which forms the model (B) of the denture base semi-finished product. Thus there is no first model of the denture base semi-finished product and no second model of the denture base. The formulations are only chosen because with them, it is always easy to differentiate and it is clarified which model is in question and in which sequence the two models (A, B) are calculated.

It is already sufficient when some key parameters of the first model (A) of the denture base are determined in order to calculate the second model (B) of the denture base semi-finished product from them. Then, the second model (B) of the denture base can be further refined. The first model (A) of the denture base does not therefore need to be complete in order to calculate the second model (B) of the denture base semi-finished product from it.

The digital three-dimensional model of the oral cavity situation of the patient can for example be recorded or have been recorded by a stereo camera, wherein the stereo camera is inserted into the oral cavity of the patient. Alternatively or in addition, a plastic impression of the oral cavity can be made which is then measured and/or recorded externally. After the recording, the data is digitalized. Here, different correction methods can be used in order to improve the quality of the data.

With the first calculation of the digital three-dimensional first model (A) of the denture base, the anatomical conditions in the oral cavity are taken into account, in order to determine a fitting denture base or several fitting denture bases, in which the chewing function of the jaw of the patient is guaranteed with the denture fitted with prosthetic teeth, or is preferably optimized. Such CAD methods are known e.g. from EP 1 444 965 A2. With such models, it is advantageous when the positions and alignments of the prosthetic teeth to be affixed in the denture base are known. In the model (A) of the denture base, recesses and/or surfaces are then provided for arranging and affixing the prosthetic teeth. Preferably, these recesses and/or surfaces are indexed in such a manner that prosthetic teeth which are accordingly indexed as a negative form can only be affixed with an unequivocal alignment on or in the denture base generated from the model (A).

As presented, within the framework of the invention, the known term "Rapid Prototyping method" is used for a production method in which the denture base semi-finished product is produced using the usual production method for Rapid Prototyping. Since the denture base semi-finished product is not a prototype, but rather a semi-finished component, instead of the term "Rapid Prototyping method", the terms occasionally used in such contexts, "Rapid Manufacturing", "generative production method", "Rapid Product Development", "Advanced Digital Manufacturing" or "E-Manufacturing" could also be used.

Methods according to the invention can also be characterized by adding volume only to surfaces of the denture base, which form the palate plate or the contact surface on the gum and the recesses or surfaces for connection of the prosthetic teeth, in order to calculate the form of the second model (B) of the denture base semi-finished product. This can in particular be advantageous when the Rapid Prototyping method used is sufficiently precise, i.e. is implemented with a precision of at least 500 µm or less than 500 µm.

With the method according to the invention, it is also recommended that when conducting the first calculation of the first model (A) of the denture base, further data is used as a basis for calculation, preferably data relating to the occlusion, position and alignment of the prosthetic teeth to be inserted, the position of a marking for aligning the denture base to the produced, data which has been obtained with the aid of a jaw template including occlusal guides, and/or data which is normally recorded on the patient in order to set an articulator.

The implementation of the first calculation of the first model (A) of the denture base is conducted in step 2).

As a result, a denture base is produced which better fits the patient. The denture base semi-finished product can for this purpose be produced to more precisely fit the denture base, since no offset volume is included for the subsequent processing of the denture base in the denture base semi-finished product, and/or must be kept available for use. The more precise the final form of the denture base is specified, the more precisely the denture base semi-finished product can be produced, as a result of which less material is used for producing the denture base semi-finished product, the tools for producing the denture base from the denture base semi-finished product are protected and the speed of producing the denture base semi-finished product and for producing the denture base from the denture base semi-finished product is increased.

With the present invention, it is also recommended that on at least one side of the denture base semi-finished product, preferably on a buccal side of the denture base semi-finished product, a holder is arranged for affixing the denture base semi-finished product on a CAM device, in particular a CAM milling machine. As a result, it can be ensured that the denture base semi-finished product can be tensioned in the correct orientation and the correct position into the CAM device in order to produce the denture base.

With methods according to the invention, it can also be provided that with the production of the denture base semi-finished product, a Rapid Prototyping method is used in which the denture base semi-finished product is produced with a degree of precision of 100 µm to 8 mm, preferably with a degree of precision 100 µm to 1 mm, particularly preferred with a degree of precision of 500 µm to 1 mm.

Such Rapid Prototyping methods are quick and relatively low-cost to implement compared to highly precise Rapid Prototyping or CAM methods.

With a further development of the invention, it can also be provided that with the production of the denture base semi-finished product, an additive Rapid Prototyping method is used, in particular 3D printing methods.

Additive Rapid Prototyping methods have the advantage that no voluminous raw bodies must be kept available for use, and only the material required for production or only slightly more than the material necessary for production is used. 3D printing methods are becoming increasingly low-cost, since the 3D printers are increasingly being offered as a mass product for end customers.

Further, it can be provided that with regard to the production of the denture base semi-finished product, one of the methods from the following list is used: Fused Layer Modeling/Manufacturing (FLM) of plastics or waxes, Fused Deposition Modeling (FDM) of plastics or waxes, in particular of acrylonitrile-butadien-styrol-copolymerisate or polylactide, Laminated Object Modeling (LOM) of plastic films, Layer Laminated Manufacturing (LLM) of plastic films, Electron Beam Melting (EBM) of plastics or waxes, Multi Jet Modeling (MJM) of waxes or plastics, in particular of thermoplasts or UV-sensitive photopolymers, polyamide casting of polyamides, Selective Laser Melting (SLM) of plastics or waxes, Selective Laser Sintering (SLS) of plastics, in particular of thermoplasts, particularly preferred of polycarbonates, polyamides or polyvinyl chloride, 3D Printing (3DP) of plastic granulate or plastic powder, Space Puzzle Molding (SPM) of plastics or waxes, Stereo Lithography (STL or SLA) of plastics or waxes, in particular of a fluid resin, duromer or elastomer, Digital Light Processing (DLP) of photopolymerizable fluid plastics, wherein the Digital Light Processing (DLP) of photopolymerizable fluid plastics and Stereo Lithography (STL or SLA) of plastics or waxes, in particular with a fluid resin, duromer or elastomer, are particularly preferred.

As a photopolymerizable fluid plastic for implementing Digital Light Processing (DLP), within the scope of the present invention, a polymethyl methacrylate plastic (PMMA plastic) is preferably used which can be polymerized with radicals and/or radically.

Further, it can be provided that the denture base semi-finished product is produced from polymethyl methacrylate (PMMA), polyether ketone (PEK), polyether ether ketone (PEEK), polyamide (PA), polycarbonate (PC) or polyurethane (PU). These materials are particularly well-suited for the subsequent processing of the denture base semi-finished product with a CAM method. Additionally, aesthetically matching denture bases can also be produced from them.

Such methods are known and can be applied effectively to the desired method for producing the denture base semi-finished product.

According to a preferred embodiment of the invention, it can be provided that the denture base semi-finished product is made of a plastic or wax, in particular a pink or gum-colored plastic, wherein as plastic, a polymethyl methacrylate (PMMA) is preferably used.

Plastics (in particular PMMA) are particularly well-suited for implementing the method and as a material for denture bases or denture base semi-finished products. The coloration can also be adapted to the conditions in the patient.

When wax is used as a material for producing the denture base, or the denture base semi-finished product, the denture base produced from wax, and/or the denture base semi-finished product produced from wax, serves only for fitting with the patient, i.e. only as a working model and not as a final denture base. The denture base produced from wax and/or the denture base semi-finished product produced from wax is used after fitting with the patient in order to produce a final denture base modeled on it.

Advantageous embodiments of the invention can be characterized by the fact that with the second calculation for calculating the digital three-dimensional second model (B) of the denture base semi-finished product, at least in sections, a distance vector to the first model (A) of the denture base is added, preferably on all sides or on each surface of the first model (A) the distance vector to the first model (A) of the denture base is added, wherein the distance vector is oriented vertically to the surface of the first model (A) and the value of the distance vector is selected between 100% and 200% to be as large as the degree of precision of the Rapid Prototyping method used, preferably selected between 100% and 150% to be as large as the degree of precision of the Rapid Prototyping method used.

Through these measures, it is achieved that the denture base semi-finished product is only thicker than the denture base to be produced at desired points, wherein the additional thickness is adapted to the degree of precision of the Rapid Prototyping method used, so that during production of the denture base from the denture base semi-finished product, as little material as possible is used.

Further, it can be provided that when calculating the second model (B) of the denture base semi-finished product, a mark on the surface of the model is included in the calculation which can be applied or is used for positioning and aligning the completed denture base semi-finished product.

With such a mark, the subsequent processing can be simplified, since the denture base semi-finished product is inserted and/or tensioned or affixed more easily or even fully automated in the desired (correct) orientation into the installation for downstream processing, or with post-processing, the denture base semi-finished product which has already been inserted and/or tensioned into the installation for downstream processing is correctly oriented in the installation.

According to a preferred embodiment of the invention, it can be provided that when calculating the second model (B) of the denture base semi-finished product, volume is added at least on the palate plate and/or the contact surface onto the dental arches of the model (A) of the denture base.

For many applications, it is sufficient when the palate plate is processed with a more precise method, such as a 4-axis mill or 5-axis mill. Through a processing of the prosthetic teeth, an occlusal adaptation can also be achieved during processing of the prosthetic teeth.

With methods according to the invention, it can already be sufficient when the surfaces of the denture base semi-finished product aside from the palate plate and/or the contact surface on the gum and the recesses or surfaces for connecting the prosthetic teeth are smoothed, insofar as the Rapid Prototyping method is sufficiently precise (a degree of precision of 500 µm should here be given as a minimum).

The objects which form the basis of the invention are also attained by means of a method for producing a denture base comprising a method according to the invention for producing a denture base semi-finished product in which following production of the denture base semi-finished product the denture base is produced using a subtractive CAM method based on the first model (A) of the denture base from which the denture base semi-finished product is produced, in particular milled.

Here, it can be provided that a subtractive CAM method uses a subtractive milling method, wherein preferably, with the subtractive milling method, a degree of precision is achieved which is greater than the degree of precision of the Rapid Prototyping method, particularly preferred, a degree of precision of at least 50 µm is achieved, very particularly preferred, a degree of precision of at least 10 µm is achieved.

Computer-controlled 4-axis mills or 5-axis mills are particularly well-suited for methods according to the invention.

With methods according to the invention for producing a denture base for producing a total denture or at least a partial denture, while applying a method according to the invention for producing a denture base semi-finished product, the following method steps can also be provided:

1) Affixing the denture base semi-finished product in a CAM device for removing material from the denture base semi-finished product with a CAM method, and 2) Removing material of the denture base semi-finished product with the CAM device on the basis of the calculated first model (A) of the denture base.

The objects of the invention are attained by a computer-controlled device for implementing a method according to the invention comprising an installation for producing the denture base semi-finished product with a Rapid Prototyping method, in particular a 3D printer for producing the denture base semi-finished product, and comprising a computer system which comprises a module for implementing the calculations of the method and a module for controlling the installation for producing the denture base semi-finished product.

With the computer system, the modules cannot be contained in a single computer, but operate on two different computer stations, wherein the computer stations must be able to transfer data for this purpose. It can here be sufficient when the data of the module for implementing the calculations of the method (or data relating to the second module (B) of the denture base semi-finished product) can be transferred to the module for controlling the installation for producing the denture base semi-finished product. Preferably, the computer system is designed with a single computer which comprises both modules.

Further, the objects which form the basis of the invention are also attained by means of a denture base semi-finished product produced using a method according to the invention for producing a denture base semi-finished product.

Finally, the objects which form the basis of the invention are also attained by means of a denture base produced using a method according to the invention for producing a denture base.

The invention is based on the surprising finding that a denture base semi-finished product can be prefabricated, so that the production of the denture base from the denture base semi-finished product can be implemented simply and quickly, wherein only a small amount of material needs to be removed from the denture base semi-finished product, or even as little as is at all possible with the Rapid Prototyping method used. For this purpose, the data can surprisingly be used which is anyway calculated or produced during the calculation of the denture base, wherein through simple addition and/or adding to the calculation of volumes to the desired points of the first model (A) of the denture base, the necessary tolerances are contained in the second model (B) of the denture base semi-finished product, and ideally not more or only slightly more than the necessary tolerances. The denture base semi-finished product is then already adapted to the respective patient and/or to their oral cavity situation, since the data measured on the patient during the calculation of the second model (B) of the denture base semi-finished product has been incorporated via the first model (A) of the denture base. The method is simple, since the precise data, which is considerably more complex to calculate, for the first model (A) of the denture base needs to be calculated anyway and is available, and as a result, the calculation of the second model (B) of the denture base semi-finished product can be achieved in a very simple manner. In the simplest case, the second model (B) of the denture base semi-finished product can be simply produced by enlarging all dimensions of the first model (A) of the denture base which run within the first model (A). For example, the first model (A) of the denture base is enclosed by a full or partial sheath, wherein the sheath has a thickness which is sufficient in order to offset all insecurities and/or imprecisions which occur during the application of the Rapid Prototyping method, and in order to offset all other additionally possible imprecisions. Through the sheath and/or the additional volume, the intention is to ensure that taking into account all eventualities which can realistically be anticipated, the volume and the form of the denture base semi-finished product is sufficient in order to mill our, cut out or carve out the desired denture base.

With the method according to the invention, it is thus possible to enable a faster and more efficient method for producing denture bases, in which the tools of the CAM device for producing the denture base from the denture base semi-finished product are protected and the loss of material can be minimized using the subtractive CAM method. The advantages of the use of denture base semi-finished products and/or methods according to the invention lie for example in the lower milling times, a lower material requirement of denture base material and a protection of the milling tools, i.e. lower wear of the milling tools compared to the use of standard milling blanks.

With the method according to the invention, the denture base semi-finished products, as well as the denture bases and dentures, are constructed in a computer-supported manner using CAD methods (CAD—Computer-Aided Design). Here, a semi-finished product of a denture base is first produced, from which a denture base is created, which later lies on the toothless or partially toothless gum of the jaw arch of a patient. If a working model has first been produced from wax, on this basis a final denture base is produced from plastic, wherein this denture base can also again be produced using a CAM method. The prosthetic teeth are then individually produced or prefabricated prosthetic teeth are individually shortened and inserted into the denture base and affixed there. The denture base which is made of plastic with the prosthetic teeth which have been set down them forms the finished denture.

Exemplary embodiments of the invention will now be described below with reference to one schematically represented FIGURE, although without restricting the invention, in which:

FIG. 1 shows an overview of the method steps according to the invention for producing a denture base 10, with which a method according to the invention for producing a denture base semi-finished product 6 is used.

In a first step, a three-dimensional image of the oral cavity of a patient 1 is recorded with an intra-oral scanner 2. The oral cavity is at least partially toothless. The intra-oral scanner 2 can be a suitable stereo camera, for example. The image data of the intra-oral scanner 2 is transferred to a computer 4 which calculates from the image information a three-dimensional digital oral cavity model of the relevant part of the oral cavity for the production of the denture.

On the basis of the oral cavity model and, if necessary of further data, such as data on the occlusion, position and alignment of the dentures to be inserted, the position of a marking for aligning the denture base to be produced, data which has been gained with the aid of a jaw template, including occlusal guides and/or data which is normally recorded on the patient in order to set an articulator, the computer 4 calculates a three-dimensional digital first model A of a denture base which fits the oral cavity situation and if necessary further parameters (such as the occlusion). The model A is shown in a broken line in FIG. 1 in order to make it clear that this is a virtual model A of the denture base, which only exists and is stored as a data quantity in the computer 4. The model A of the denture base contains no dentures, which are only added later, the position, alignment and form of which have however already been taken into account in the calculation of the first model A of the denture base. The model A of the denture base can therefore already contain recesses, indentations and/or contact surfaces, for example, for holding and/or connecting dentures.

As a next step, a digital three-dimensional second model B of the denture base semi-finished product is calculated using the computer 4 from the digital three-dimensional first model A of the denture base. For this purpose, volume is added on all surfaces of the first model 2 of the denture base. The model B is also shown in a broken line in FIG. 1 in order to make it clear that this is a virtual model B of the denture base semi-finished product, which only exists and/or is stored as a data quantity in the computer 4. The first model A of the denture base can thus be fully incorporated by the second model B of the denture base semi-finished product. In particular, volume is added on the underside of the model A of the denture base, which forms the contact surface for the toothless jaw col and/or the gum (shown in FIG. 1 below).

Based on the second model B of the denture semi-finished product, with the aid of the computer 4 and/or controlled by the computer 4, a real denture base semi-finished product 6 is produced from a plastic or a wax with the aid of a 3D printer 8 or another installation 8 for implementing a Rapid Prototyping method. The plastic has the pink color of gums. The denture base semi-finished product 6 thus produced is then tensioned into a 5-axis or 4-axis mill 12 or another device for implementing a subtractive and highly precise CAM method, and on the basis of the first model A of the denture base, a real denture base 10 is milled out of the denture base semi-finished product 6. The 5-axis or 4-axis mill 12 operates considerably more precisely, but also more slowly, than the 3D printer 8. While therefore the rough form is produced as a denture base semi-finished product 6 with the fast but imprecise 3D printer, the subsequent precision work is conducted using the 5-axis or 4-axis mill 12. The 5-axis or 4-axis mill 12 is also controlled by the computer 4 or by another control unit (not shown) on the basis of the first model A of the denture base.

Due to the fact that the second model B of the denture base semi-finished product is produced on the basis of the first model A of the denture base or on the basis of data which is also decisive for producing the first model A of the denture base, the use of material can be minimized, as can the time needed for producing the denture base in the 5-axis or 4-axis mill 12. As a result, the consumption of plastic or wax and the wear of the milling head of the 5-axis or 4-axis mill is reduced and the method is accelerated.

The features of the invention disclosed in the above description, and in the claims, FIGURES and exemplary embodiments, can be essential both individually and in any combination required for the realization of the invention in its different embodiments.

LIST OF REFERENCE NUMERALS

1 Patient
2 3D intra-oral scanner
4 Computer
6 Denture base semi-finished product
8 3D printer/installation for implementing a Rapid Prototyping method
10 Denture base
12 CAM-controlled 5-axis or 4-axis mill
A Model of the denture base
B Model of the denture base semi-finished product

The invention claimed is:

1. A method for fabricating a denture base semi-finished product to be subsequently formed into a pink- or gum-colored plastic or wax denture base by subtractive milling of the denture base semi-finished product, the method comprising the following steps:
   (a) recording and digitalizing an at least partially toothless oral cavity situation of a patient to produce a digital three-dimensional oral cavity model of the patient, or providing a digital three-dimensional oral cavity model of the at least partially toothless oral cavity situation of the patient;
   (b) conducting a first calculation in which a digital three-dimensional first model of the denture base is calculated, wherein the denture base will be a part of a full or partial denture in which separately-produced prosthetic teeth are to be inserted, and wherein the digital three-dimensional oral cavity model of (a) is used as a basis for the first calculation, and wherein the digital three-dimensional first model of the denture base provides one or more of a palate plate, surfaces on dental arches, and recesses and/or surfaces for arranging and affixing the prosthetic teeth in the denture base, which recesses and/or surfaces are calculated from positions and alignments of prosthetic teeth to be affixed in the denture base;
   (c) conducting a second calculation in which a digital three-dimensional second model of a denture base semi-finished product is calculated from the digital three-dimensional first model of the denture base of (b) by adding volume to the digital three-dimensional first model of the denture base of (b) at least in sections corresponding to at least one of the palate plate, the surfaces on dental arches, and the recesses and/or surfaces for connecting the prosthetic teeth using a CAD (computer-aided design) method; and
   (d) fabricating the denture base semi-finished product from a pink- or gum-colored plastic or a wax using a CAM (computer-aided manufacturing) Rapid Prototyping method based on the digital three-dimensional second model of the denture semi-finished product of (c) wherein the denture base semi-finished product has dimensions corresponding to the volume of the second model of the denture base semi-finished product according to step (c).

2. The method according to claim 1, comprising, when conducting the first calculation of the digital three-dimensional first model of the denture base of (b), using further data as a basis for calculation.

3. The method according to claim 1, comprising, during the fabrication of the denture base semi-finished product, using a Rapid Prototyping method in which the denture base semi-finished product is fabricated with a degree of precision of 100 μm to 8 mm.

4. The method according to claim 1, comprising, during fabrication of the denture base semi-finished product, using an additive Rapid Prototyping method.

5. The method according to claim 1, comprising, during the fabrication of the denture base semi-finished product, using a method selected from the group consisting of:
   Fused Layer Modeling/Manufacturing (FLM) of plastics or waxes, Fused Deposition Modeling (FDM) of plastics or waxes, Laminated Object Modeling (LOM) of plastic films, Layer Laminated Manufacturing (LLM) of plastic films, Electron Beam Melting (EBM) of plastics or waxes, Multi Jet Modeling (MJM) of waxes or plastics, polyamide casting of polyamides, Selective Laser Melting (SLM) of plastics, Selective Laser Sintering (SLS) of plastics or waxes, 3-D-Printing (3DP) of plastic granulate or plastic powder, Space Puzzle Molding (SPM) of plastics or waxes, Stereo Lithography (STL or SLA) of plastics or waxes, and Digital Light Processing (DLP) of photopolymerizable fluid plastics.

6. The method according to claim 3, comprising, with the second calculation for calculating the digital three-dimensional second model of the denture base semi-finished product of (c), adding, at least in sections, a distance vector to the digital three-dimensional first model of the denture base of (b), wherein the distance vector is oriented vertically with respect to a surface of the digital three-dimensional first model of (b) and a value of the distance vector is selected between 100% and 200% compared to the degree of precision of the Rapid Prototyping method.

7. The method according to claim 1, comprising, when calculating the digital three-dimensional second model of the denture base semi-finished product of (c), including a mark on a surface of the model in the calculation which is applicable or is used for positioning and aligning the completed denture base semi-finished product.

8. The method according to claim 1, comprising, when calculating the digital three-dimensional second model of the denture base semi-finished product of (c), adding volume at least on a palate plate and/or contact surface onto dental arches of the digital three-dimensional first model of the denture base of (b).

9. A method for fabricating a denture base comprising a method for fabricating a denture base semi-finished product according to claim 1, further comprising, following fabrication of the denture base semi-finished product, fabricating the denture base from the denture base semi-finished product using a subtractive CAM (computer-aided manufacturing) method based on the digital three-dimensional first model of the denture base of (b).

10. The method according to claim 9, comprising using a subtractive milling method as a subtractive CAM (computer-aided manufacturing) method.

11. A computer-controlled device for implementing a method according to claim 1, comprising an installation for fabricating the denture base semi-finished product with a Rapid Prototyping method, and comprising a computer system which comprises a module for implementing the calculations of the method and a module for controlling the installation for fabricating the denture base semi-finished product.

12. A denture base semi-finished product fabricated using a method according to claim 1.

13. A denture base fabricated using a method according to claim 9.

14. The method according to claim 2, wherein the further data relate to occlusion, position, and alignment of the prosthetic teeth to be inserted, the position of a marking for aligning the denture base to be produced, data which have been obtained with the aid of a jaw template including occlusal guides, and/or data which are normally recorded on the patient to set an articulator.

15. The method according to claim 3, wherein the degree of precision is 100 µm to 1 mm.

16. The method according to claim 3, wherein the degree of precision is 500 µm to 1 mm.

17. The method according to claim 4, comprising, during fabrication of the denture base semi-finished product, using a 3D (three-dimensional) printing method.

18. The method according to claim 5, comprising, during the fabrication of the denture base semi-finished product, using a method selected from the group consisting of:

Fused Deposition Modeling (FDM) of acrylonitrile butadiene styrene or polylactide, Multi Jet Modeling (MJM) of thermoplasts or UV (ultraviolet)-sensitive photopolymers, Selective Laser Sintering (SLS) of thermoplasts, Stereo Lithography (STL or SLA) of fluid resin, duromer, or elastomer, and Digital Light Processing (DLP) of photopolymerizable fluid plastics.

19. The method according to claim 18, comprising, during the fabrication of the denture base semi-finished product, using a method selected from the group consisting of:

Selective Laser Sintering (SLS) of polycarbonates, polyamides, or polyvinyl chloride thermoplasts, Digital Light Processing (DLP) of photopolymerizable fluid plastics, and Stereo Lithography (STL or SLA) of a fluid resin, duromer or elastomer.

20. The method according claim 1, wherein the denture base semi-finished product is made of a pink- or gum-colored plastic.

21. The method according claim 20, wherein the pink- or gum-colored plastic is a polymethyl methacrylate (PMMA).

22. The method according to claim 6, comprising, with the second calculation for calculating the digital three-dimensional second model of the denture base semi-finished product of (c), adding, on all sides or on each surface of the digital three-dimensional first model of a denture base of (b), the distance vector to the digital three-dimensional first model of the denture base of (b).

23. The method according to claim 6, wherein the value of the distance vector is selected between 100% and 150% compared to the degree of precision of the Rapid Prototyping method.

24. A method for fabricating a denture base comprising a method for fabricating a denture base semi-finished product according to claim 9, comprising, following fabrication of the denture base semi-finished product, fabricating the denture base by milling.

25. The method according to claim 10, wherein with the subtractive milling method, a degree of precision is achieved which is greater than a degree of precision of the Rapid Prototyping method.

26. The method according to claim 25, wherein a degree of precision of at least 50 µm is achieved.

27. The method according to claim 25, wherein a degree of precision of at least 10 µm is achieved.

28. A computer-controlled device for implementing a method according to claim 11, wherein the installation for fabricating the denture base semi-finished product with a Rapid Prototyping method is a 3D (three-dimensional) printer.

29. The method of claim 1, wherein step (c) comprises conducting a second calculation in which a digital three-dimensional second model of a denture base semi-finished product is calculated from the digital three-dimensional first model of the denture base of (b) by adding volume to the digital three-dimensional first model of the denture base of (b) only in sections corresponding to one or more of the palate plate, the surfaces on dental arches, and the recesses and/or surfaces for connecting the prosthetic teeth using a CAD (computer-aided design) method.

* * * * *